US009877922B2

(12) United States Patent
Lee et al.

(10) Patent No.: US 9,877,922 B2
(45) Date of Patent: Jan. 30, 2018

(54) PROCESS OF PREPARING MICROSPHERES FOR SUSTAINED RELEASE HAVING IMPROVED DISPERSIBILITY AND SYRINGEABILITY

(75) Inventors: Hee-Yong Lee, Daejeon (KR); Jung-Soo Kim, Daejeon (KR); Eun-Ho Shin, Daejeon (KR); Seong-Kyu Kim, Daejeon (KR); Eun-Young Seol, Daejeon (KR); Mi-Jin Baek, Daejeon (KR); Mi-Young Baek, Daejeon (KR); Yeon-Jin Chae, Daejeon (KR); Ho-Il Choi, Daejeon (KR); Juhan Lee, Daejeon (KR)

(73) Assignees: Peptron Co., Ltd., Daejeon (KR); Daewoong Pharmaceutical Co., Ltd., Kyunggi-Do (KR)

( * ) Notice: Subject to any disclaimer, the term of this patent is extended or adjusted under 35 U.S.C. 154(b) by 531 days.

(21) Appl. No.: 12/429,523

(22) Filed: Apr. 24, 2009

(65) Prior Publication Data
US 2009/0269414 A1   Oct. 29, 2009

Related U.S. Application Data

(63) Continuation-in-part of application No. 11/511,951, filed on Aug. 29, 2006, now abandoned.

(30) Foreign Application Priority Data

May 11, 2006   (KR) .......................... 10-2006-0042462

(51) Int. Cl.
  *A61K 9/16*     (2006.01)
  *A61K 38/09*    (2006.01)
  *A61K 38/31*    (2006.01)
  *A61K 31/765*   (2006.01)

(52) U.S. Cl.
  CPC .......... *A61K 9/1647* (2013.01); *A61K 9/1635* (2013.01); *A61K 9/1694* (2013.01); *A61K 31/765* (2013.01); *A61K 38/09* (2013.01); *A61K 38/31* (2013.01)

(58) Field of Classification Search
  None
  See application file for complete search history.

(56) References Cited

U.S. PATENT DOCUMENTS

| | | | |
|---|---|---|---|
| 4,389,330 A | 6/1983 | Tice | |
| 4,652,441 A | 3/1987 | Okada | |
| 4,673,595 A | 6/1987 | Orsolini | |
| 4,711,782 A | 12/1987 | Okada | |
| 4,954,298 A | 9/1990 | Yamamoto | |
| 5,061,492 A | 10/1991 | Okada | |
| 5,134,122 A | 7/1992 | Orsolini | |
| 5,192,741 A | 3/1993 | Orsolini | |
| 5,225,205 A | 7/1993 | Orsolini | |
| 5,330,767 A | 7/1994 | Yamamoto | |
| 5,431,348 A | 7/1995 | Orsolini | |
| 5,439,688 A | 8/1995 | Orsolini | |
| 5,445,832 A | 8/1995 | Orsolini | |
| 5,476,663 A | 12/1995 | Okada | |
| 5,480,656 A | 1/1996 | Okada | |
| 5,611,971 A | 3/1997 | Maedera | |
| 5,622,657 A | 4/1997 | Takada | |
| 5,631,020 A | 5/1997 | Okada | |
| 5,631,021 A | 5/1997 | Okada | |
| 5,741,478 A | 4/1998 | Osborne | |
| 5,776,885 A | 7/1998 | Orsolini | |
| 5,945,126 A | 8/1999 | Thanoo | |
| 6,190,700 B1 | 2/2001 | Okada et al. | |
| 2004/0097419 A1 | 5/2004 | Petersen et al. | |
| 2004/0121003 A1 | 6/2004 | Chickering, III | |

(Continued)

FOREIGN PATENT DOCUMENTS

| | | |
|---|---|---|
| EP | 0052510 A2 | 5/1982 |
| IE | 920956 | 7/1992 |
| KR | 100177309 B1 | 11/1998 |

(Continued)

OTHER PUBLICATIONS

Flandroy et al ('(D,L)Polylactide microspheres as embolic agent' Neuroradiology v32 1990 pp. 311-315).*
Freitas et al ('Microencapsulation by solvent extraction/evaporation: reviewing the state of the art of microsphere preparation process technology' Journal of Controlled Release v102 2005 pp. 313-332).*
Schwegman et al ('Practical formulation and process development of freeze-dried products' Pharmaceutical Development and Technology v10 2005 pp. 151-173).*
English Translation of Abstract for KR Patent Application No. 100177309 B1; Publication Date: Nov. 17, 1998; Applicant: LG. Philips LCD Co., Ltd. (2 pgs.).
English Translation of Abstract for KR Patent Application No. 1020030081179 A; Publication Date: Oct. 17, 2003; Applicant: Daewoong Co., Ltd., et al. (1 pg.).

(Continued)

*Primary Examiner* — Karlheinz R. Skowronek
*Assistant Examiner* — Ronald T Niebauer
(74) *Attorney, Agent, or Firm* — Cesari and McKenna, LLP (57) ABSTRACT

Disclosed is a process of preparing sustained release microspheres, containing a biodegradable polymer as a carrier and a drug, using spray drying. The process comprises preparing a solution, suspension or emulsion containing a biodegradable polymer, a drug and a solvent; spray drying the solution, suspension or emulsion; and suspending spray-dried microspheres in an aqueous solution containing polyvinyl alcohol to remove the residual solvent and increase the hydrophilicity of the microsphere surface. The process enables the preparation of microspheres having high drug encapsulation efficiency, almost not having a toxicity problem due to the residual solvent, and having good syringeability. The microspheres prepared according to the present invention release an effective concentration of a drug in a sustained manner for a predetermined period when administered to the body, and are thus useful in the treatment of diseases.

1 Claim, 2 Drawing Sheets

(56) References Cited

U.S. PATENT DOCUMENTS

2005/0261195 A1   11/2005   Sasaki et al.
2007/0264341 A1*  11/2007   Lee et al. .................... 424/486

FOREIGN PATENT DOCUMENTS

| KR | 1020030081179 A | 10/2003 |
| WO | 200130320 A1 | 5/2001 |
| WO | 2004112752 A1 | 12/2004 |
| WO | WO 2004/112752 * | 12/2004 |
| WO | 2005023224 A1 | 3/2005 |
| WO | WO-2005/110369 A2 | 11/2005 |

OTHER PUBLICATIONS

Shameem M, Lee Hee Yong, DeLuca P.P., "Short-term (Accelerated release) Approach to Evaluate Peptide Release from PLGA Depot Formulations" (1999) AAPS Pharmsci., 1(3) article7.

Kostanski J.W., (2000) "Preparation, Characterization, and In Vitro Evaluation of 1- and 4-month Controlled Release Orntide PLA and PLGA Microspheres" Pharm Dev. Tech 5,4 p. 585-596.

Okada, H. and Toguchi, H., (1995) "Biodegradable Microspheres in Drug Delivery" Crit. Rev. Ther Drug Carrier Syst., 12,p. 1-99.

D. Ermis, A. Yuksel, (1999) "Preparation of Spray-dried microspheres of indomethacin and examination of the effects of coating on dissolution rates" J. Microencapsulation, vol. 16, No. 3, p. 315-324.

Hueper, W.C., (1959) "Carcinogenic Studies on Water-Soluable and Insoluable Macromolecules" Archives of Pathology, vol. 67, June p. 589-617.

Shameem et al., "A Short-term (accelerated release) approach to evaluate peptide release from PLGA Depot Formulations." AAPS 1999, 1(3) Article 7.

Sahoo, Sanjeeb K. et al., "Residual polyvinyl alcohol associated with poly (D,L-lactide-coglycolide) nanoparticles affects their physical properties and cellular uptake," Journal of Controlled Release 82 (2002) 105-114.

* cited by examiner

↑ challenge  100 ug/kg as leuprolide acetate
⇑ second administration

Figure 3

PROCESS OF PREPARING MICROSPHERES FOR SUSTAINED RELEASE HAVING IMPROVED DISPERSIBILITY AND SYRINGEABILITY

CROSS REFERENCE TO RELATED APPLICATIONS

This application is a continuation-in-part of U.S. patent application Ser. No. 11/511,951, filed Aug. 29, 2006, now abandoned, which claims the benefit of Republic of Korea Patent Application Serial No.: 10-2006-0042462, filed May 11, 2006, both of which are herein incorporated by reference in their entirety.

TECHNICAL FIELD

The present invention relates to a process of preparing sustained release microspheres comprising a biodegradable polymer as a carrier and a drug. Such microspheres are an injectable sustained-release formulation, which enables the sustained and uniform release of a drug so as to maintain its biological activity in the body upon subcutaneous or intramuscular injection.

BACKGROUND ART

A number of approaches have been used to encapsulate bioactive agents into microspheres of polymers for sustained release. Most of them are based on phase separation (U.S. Pat. No. 4,673,595, EP 52,510), cryopulverization after melt extrusion (U.S. Pat. Nos. 5,134,122, 5,192,741, 5,225,205, 5,431,348, 5,439,688, 5,445,832 and 5,776,885), double emulsion evaporation (w/o/w, water/oil/water) (U.S. Pat. Nos. 4,652,441, 4,711,782, 4,954,298, 5,061,492, 5,330,767, 5,476,663, 5,480,656, 5,611,971, 5,631,020 and 5,631,021), single emulsion evaporation (o/w, oil/water) (U.S. Pat. Nos. 4,389,330 and 5,945,126; Shameem M, Lee Hee Yong, DeLuca P. P., AAPS Pharmsci., 1 (3) article 7, 1999; Kostanski J. W., Pharm. Dev. Tech. 5, 585-596, 2000), and spray drying (IE920956).

Phase separation method is a process for preparing microspheres in which a biodegradable polymer is dissolved in an excessive amount of an organic solvent, such as methylene chloride, and a drug dissolved in a small amount of water is added to the polymer solution with stirring. Silicon oil is then added to the polymer-drug mixture at a constant rate to form embryonic microspheres, and an excessive amount of a non-solvent, such as trichlorofluoromethane, is added to the solution to extract the organic solvent from the embryonic microspheres. The solidified microspheres are recovered by filtration, and dried under pressure. However, the phase separation method is problematic as follows. Since the toxic solvent such as methylenechloride is not sufficiently removed by drying under pressure, the residual solvent reduces the stability of formulations, and may also be detrimental to health when administered to the body. Also, the excessive use of non-solvent, such as freon, hexane, heptane, cyclohexane, and trichlorofluoromethane, for the solidification of embryonic microspheres is not cost-effective upon mass production and causes serious environmental contamination.

By contrast, cryopulverization after melt extrusion permits minimal use of toxic solvents. This method is a process for preparing microspheres in which a mixture of a biodegradable polymer and a drug is melt-extruded through an extruder at a high temperature and pulverized at a low temperature. The biodegradable polymer-drug mixture may be obtained by homogeneously mixing a polymer and a drug in a solvent, such as methylene chloride, with an agitator, and removing the organic solvent using a rotary evaporator or a vacuum dryer, or by cryo-milling at a low temperature and sieving each powder and blending the two fine powders. The latter case does not have the problem of the residual toxic solvent because it does not employ a toxic solvent during microsphere preparation. However, the procedure for preparing microparticles does not exclude the possibility of an interaction between the polymer and the drug and denaturation of the drug due to high temperature and high pressure upon melt-extrusion, and denaturation of the drug due to heat locally generated during cryopulverization. This method is also difficult to use to make microspheres having a uniform size, which are thus easy to inject.

The two methods for preparing microspheres, in addition to the problems of residual solvent, difficulty in mass production and drug denaturation, have another disadvantage in that a biodegradable polymer used for the sustainable release of a drug is non-hydrophilic and thus poorly dispersible in an aqueous suspension for injection.

Water-in-oil-in-water (w/o/w) double emulsion evaporation has commonly been applied to encapsulate hydrophilic drugs, such as peptides or proteins, into polymeric microspheres. In this W/O/W method, a hydrophilic drug is dissolved in water, and this aqueous phase is dispersed in an organic phase containing a biodegradable polymer to yield a primary emulsion (water in oil). This primary emulsion is again dispersed in a secondary aqueous phase containing an emulsifier. Single emulsion evaporation (oil in water (o/w)) has been commonly used in the encapsulation of lipophilic drugs. In this O/W method, a drug and a biodegradable polymer are co-dissolved in a mixture of suitable organic solvents (e.g., methanol and methylene chloride), and the resulting solution is dispersed in an aqueous phase. In both emulsion evaporation methods, as an organic solvent is removed by extraction or evaporation during polymer dispersion in an aqueous phase, the polymer decreases in solubility and is thus solidified to form microspheres. In these methods, the technically important factor is the encapsulation efficiency of bioactive drugs.

Most hydrophilic drugs leak in large amounts when dispersed in an aqueous phase, resulting in low encapsulation efficiency. To solve this problem, Okada et al. employed material such as gelatin in the microsphere preparation based on double emulsion evaporation. This material increased the viscosity of a primary emulsion and decreased the diffusion rate of a drug (an LHRH derivative) into a secondary emulsion, resulting in enhanced drug encapsulation (Okada, H. and Toguchi, H., Crit. Rev. Ther. Drug Carrier Syst., 12, 1-99, 1995). Similarly, the single emulsion evaporation method also can enhance drug encapsulation by suitably increasing the concentration of a biodegradable polymer (PLGA) dissolved in an organic solvent phase. Typically, microspheres prepared by double emulsion evaporation are more porous than those prepared by single emulsion evaporation, and thus have increased surface areas, leading to a relatively high initial release rate of a drug.

However, the single and double emulsion evaporation methods for preparing microspheres, like the phase separation method, have the following disadvantages: difficulty in the removal of an organic solvent used for dissolving a biodegradable polymer, difficulty in mass production procedures due to changes in solvent removal rate, allergic reactions to gelatin used for increasing the viscosity of a primary emulsion, the possibility of a drug becoming denatured and losing its activity due to strong shearing force applied for making small microspheres during primary emulsion preparation, limited drug encapsulation, and the like.

The spray drying method has also been used for preparing finely atomized particles. In this method, typically, a solution of a material to be dried, or a suspension or emulsion in which a biodegradable polymer and a drug are homogenously dissolved, is supplied to a nozzle, sprayed through the nozzle, and exposed to heated air to evaporate the solvent used. In particular, in the case of preparing sustained release microspheres, the drug release rates of prepared microspheres greatly depend on the composition or content of a biodegradable polymer, the type or content of an additive, the composition of a solvent, and the like. In addition to the above processing parameters, other parameters affecting the morphology, size or properties of microspheres may be employed to control the release rates of drugs, the parameters including the type of a spray nozzle through which a spray solution is sprayed (for example, a type that atomizes droplets using compressed air, a type that atomizes droplets using centrifugal force when a spray solution flows into a disc rotating at a high speed, a type that atomizes droplets using ultrasonic waves generated when a vibrator vibrates, etc.), supply rate of a spray solution, and temperature, supplied amount and supply rate of drying air. In addition, the spray drying method, unlike other methods for preparing sustained release microspheres, is advantageous in that it provides a continuous process, which facilitates microsphere production and thus conversion from small-scale to large-scale production.

Although the spray drying method has the advantage of permitting large-scale production of microspheres, it has disadvantages as follows. The solvent used is not sufficiently removed merely by spray drying. The residual solvent causes a problem in the stability of the biodegradable polymer upon long-term storage, leading to changes in drug release profiles of microspheres. Another disadvantage of this method is that since biodegradable polymers used for drug encapsulation are mostly non-hydrophilic, microspheres prepared are not suspended well and are thus difficult to accurately administer.

As described above, most conventional methods of preparing sustained release microspheres employ a toxic solvent, and have problems including residue of the toxic solvent used, the microsphere size not being suitable for injection, poor suspendability of microspheres, and difficult mass production.

The present inventors intended to provide a process for preparing bioactive drug-loaded biodegradable polymer microspheres, which are easy for mass production, by solving the aforementioned problems.

DISCLOSURE OF THE INVENTION

It is therefore an object of the present invention to provide a process for preparing sustained release microspheres comprising a biodegradable polymer as a carrier and a bioactive drug, the microspheres being easy for mass production, not containing a residual toxic solvent, which is a problem of conventional methods of preparing sustained release microspheres, having high drug encapsulation efficiency, and having a uniform size suitable for injection.

The present inventors conducted intensive studies, and found that when microspheres, which are obtained by spray drying a solution, suspension or emulsion containing a biodegradable polymer, a drug and a solvent, are suspended in an aqueous solution containing polyvinyl alcohol to remove the residual solvent, the microspheres have improved suspendability and syringeability and high drug encapsulation efficiency with almost no residual toxic solvent, thereby leading to the present invention.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

The present invention relates to a process of preparing sustained release microspheres, in which a solution, suspension or emulsion containing a biodegradable polymer, a drug and a solvent is spray dried, and microspheres thus obtained are dispersed in an aqueous solution containing polyvinyl alcohol, thereby more easily removing residual solvent and improving suspendability of the microspheres upon administration.

In detail, the present invention relates to a process of preparing sustained release microspheres having high drug encapsulation efficiency, almost no residual solvent, and improved suspendability by dissolving and spray drying a biodegradable polymer and a drug, suspending microspheres thus obtained in an aqueous solution in which polyvinyl alcohol is dissolved, and recovering, washing and freeze drying the microspheres.

In one aspect, the present invention provides a process of preparing sustained release microspheres, comprising spraying a solution, suspension or emulsion containing a biodegradable polymer, a drug and a solvent into a dry chamber and drying it using drying air to remove the solvent; and dispersing spray-dried microspheres in an aqueous solution containing polyvinyl alcohol to remove the residual solvent and improve dispersibility of the microspheres.

The term "biodegradable polymer," as used herein, refers to a polymer that slowly degrades when administered to the body, and is thus not harmful to the body. Examples of such polymers include polylactide (PLA), polyglycolide (PGA) and their copolymer, poly(lactide-co-glycolide) (PLGA), polyorthoester, polyanhydride, polyhydroxybutyric acid, polycaprolactone, polyalkylcarbonate, and derivatives thereof.

The term "drug," as used herein, includes peptides having biological activities, such as anticancer agents, antibiotics, antipyretics, analgesics, anti-inflammatory agents, antitussive expectorants, sedatives, antiulcer agents, antidepressants, antiallergenic agents, antidiabetic agents, antihyperlipidemic agents, antituberculous agents, hormonal agents, bone metabolic agents, immunosuppressors, angiogenesis inhibitors, contraceptives, and vitamin-like agents. In particular, biologically active peptide or protein drugs are preferred. Examples of oligopeptides having biological activities include insulin, somatostatin and derivatives thereof, growth hormone, prolactin, adrenocorticotropic hormone, melanocyte-stimulating hormone, thyrotropin-releasing hormone and salts and derivatives thereof, thyroid-stimulating hormone, luteinizing hormone, follicle-stimulating hormone, vasopressin and derivatives thereof, oxytocin, calcitonin, parathyroid hormone, glucagon, gastrin, secretin, pancreozymin, cholecystokinin, angiotensin, human placental lactogen, human chorionic gonadotropin, and enkephalin and derivatives thereof. Examples of polypeptides include endorphin, interferon (α-type, β-type, γ-type), interleukin, tuftsin, thymopoietin, thymosin, thymostimulin, thymic humoral factor (THF), serum thymic factor and derivatives thereof, tumor necrosis factor, colony stimulating factor (CSF), motilin, dynorphin, bombesin, neurotensin, bradykinin, caerulein, urokinase, asparaginase, kallikrein, substance P, nerve growth factor, blood coagulation factor VIII and IX, lysozyme, polymyxin B, colistin, gramicidin, bacitracin, protein synthesis-stimulating peptide, vasoactive intestinal polypeptide, platelet-derived growth factor, growth hormone-releasing factor, bone morphogenetic protein, epidermal growth factor, and erythropoietin.

In the present invention, the aqueous solution containing polyvinyl alcohol is used to more effectively remove the residual solvent inside microspheres immediately after spray drying and to disperse microspheres well in an injection solution upon administration. This aqueous solution is removed through an additional washing step, and polyvinyl alcohol finally remains in microspheres at an amount less than 1%.

The "glass transition temperature," or "Tg," is the temperature at which the amorphous domains of a polymer change from a brittle vitreous state to a solid deformable or ductile state at atmospheric pressure. In other words, the Tg corresponds to the temperature at which the onset of segmental motion in the chains of the polymer occurs. The glass transition temperature is related to the temperature or temperature range at which there is a fundamental change in the physical properties of the polymer. This change does not reflect a change in state, but rather a change in the macromolecular mobility of the polymer. Below the Tg, the polymer chain mobility is severely restricted. The glass transition temperature "Tg" of the polymers can be easily measured, for example, by known methods (for example, Dieter Bendix, polymer degradation and stability 59 (1998) 129-135, U.S. Pat. No. 6,543,931), and Tg values of many known polymers are published. For example, polylactide and poly(lactide-co-glycolide) which is one of the polymer materials used in the present invention is known to have a Tg value of 40~60° C. typically.

The preferable temperature of the suspension is below the Tg of the biodegradable polymer. If the suspension temperature is higher than the Tg of the polymer, the drug loss becomes significantly high during the suspension process. Another disadvantage of using a temperature higher than Tg is a difficulty in maintaining the drug content of the microsphere at a consistent level due to the fast release of the drug from the microsphere during the suspension process.

Using this feature, when microspheres are suspended in the aqueous solution of polyvinyl alcohol to remove the residual solvent, the removal speed of the residual solvent may be controlled by altering the temperature of the suspension. Upon small-scale production, the residual solvent may be removed within a short time at the temperature between room or ambient to Tg of the biodegradable polymer used. Upon large-scale production, the suspension is maintained at low temperature to remove the residual solvent at a slow speed, thereby preventing deterioration of products due to extended handling time of large quantities of products.

In an additional dispersion step, the content of polyvinyl alcohol in the aqueous solution is preferably 0.01-20% (w/v), and more preferably 0.05-10% (w/v). Polyvinyl alcohol has a molecular weight of 3,000 to 300,000, preferably 5,000 to 100,000, and has a hydration rate of 75% to 95%. The amount of polyvinyl alcohol remaining on the surface of microspheres is preferably 0.02-1% (w/w), and more preferably 0.05-0.5% (w/w).

The term "solvent," as used herein, refers to a material that is able to dissolve a biodegradable polymer and/or a drug. An appropriate solvent may be selected by those having ordinary skill in the art according to the type of biodegradable polymer. Glacial acetic acid is preferred.

The present invention includes a step of dispersing microspheres in an aqueous solution of polyvinyl alcohol to improve the dispersibility of microspheres. The dispersion step is carried out for about one minute or longer to achieve maximal effects. The preferred dispersion time is 5 min or longer.

In a patent application filed prior to the present invention (Korean Pat. Application 10-2003-0023130), the present inventors improved drug encapsulation efficiency and release profiles of microspheres by homogenously dissolving a biodegradable polymer and a drug using a non-toxic solvent and spray drying the resulting solution, and suggested a spray drying method facilitating the mass production of microspheres. This spray drying method has advantages including easy mass production, low residual solvent, high drug encapsulation efficiency, and ideal drug release profiles, but has drawbacks including difficult dispersion and suspension of sustained release microspheres obtained by spray drying in an injection solution due to non-hydrophilicity of a polymer contained in the microspheres, and requirement of an additional step for removing the residual solvent to ensure the stability of microspheres upon long-term storage. Thus, the present inventors intended to solve these disadvantages in the present invention.

A conventional method of preparing microspheres by spray-drying using two nozzles is disclosed in U.S. Pat. No. 5,622,657. To improve the dispersibility of polymeric microspheres, which are apt to adhere to each other or aggregate when prepared by spray drying, the cited invention provides a method of coating drug-loaded polymeric microspheres with an aggregation-preventing agent using two or more nozzles, in which a polymer solution containing a biologically active substance and an aqueous solution of an agent for preventing aggregation of microparticles are sprayed separately from different nozzles at the same time. A similar method is disclosed in Korean Pat. No. 0177309, the method being characterized by spraying a dispersion in which a water-soluble dispersing agent is dissolved in the direction opposite to the spraying direction of a biodegradable polymer solution containing an active ingredient and the flow direction of drying air in order to coat a portion or all of sustained release microparticles with the water-soluble dispersing agent. The cited inventions intended to prevent microspheres from aggregating by spraying an aqueous solution for preventing microsphere aggregation immediately after microspheres are formed using spray drying, but there are following disadvantages. Since microspheres are coated with an aggregation-preventing agent immediately after being spray dried, a toxic solvent used for dissolving a polymer for preparing microspheres remains in microspheres in large quantities. In addition, when microspheres are suspended in an injection solution for administration, an excess amount of a dispersing agent is used. Moreover, aggregation-preventing agents used in the cited inventions, such as hydroxypropylcellulose, carboxymethylcellulose, glycin, alanin, gelatin and collagen, do not improve the suspendability in an injection solution or the syringeability, resulting in non-uniform dosages.

On the other hand, in order to enhance the fluidity of granules for tablet preparation or drug particles and improve the solubility of drugs, a water-soluble dispersing agent, such as hydroxypropylmethylcellulose, hydroxypropylcellulose, and polyvinyl alcohol, may be spray dried together with a drug to be contained in the resulting preparation in an amount of about 4 to 19 wt % (D. Ermis, A. Yuksel, Preparation of spray-dried microspheres of indomethacin and examination of the effects of coating on dissolution rates, J. Microencapsulation, vol. 16, No. 3, 3,315-324 (1999)). In the literature, the water-soluble dispersing agents are used to enhance the solubility of poorly water-soluble drugs, thereby dissolving the drugs within several hours, and increase the fluidity of drug particles, thereby facilitating processing such as tabletting. Polyvinyl alcohol has been registered as a material liable to induce cancer when parenterally administered to animals, and thus the residual amount thereof should be controlled (Carcinogenic Studies on Water-Soluble and Insoluble Macromolecules, Archives of Pathology, 67, 589-617, 1959). The present inventors found that when polyvinyl alcohol, suspended in a polymer solution, is sprayed as described in the above literature, the content of polyvinyl alcohol, which is difficult to degrade in the body, increases, and the initial drug release greatly increases. Such a high initial drug release may cause side effects, and may lead to a reduced drug release duration, thereby not guaranteeing suitable therapeutic effects.

The present inventors prepared microspheres in which the residual solvent is additionally removed and which have improved syringeability, through a process comprising preparing microspheres using a spray drying method developed by the present inventors prior to the present invention, suspending the microspheres in an aqueous solution containing polyvinyl alcohol, and washing and recovering the microspheres.

The process of preparing biodegradable polymer microspheres containing a drug having biological activity according to the present invention comprises preparing microspheres by spray drying, suspending the microspheres thus obtained in an aqueous solution containing polyvinyl alcohol, and recovering, washing and drying the microspheres, allows further removal of the residual solvent and improves the suspendability of microspheres upon administration, thereby leading to accurate administration of drugs and effective treatment of diseases.

A better understanding of the present invention may be obtained through the following examples which are set forth to illustrate, but are not to be construed as the limit of the present invention.

Preparation Example 1: Preparation of Microspheres and a Post-Process Using Various Dispersing Agents PLGA microspheres were prepared using a spray dryer (SODEVA, France) equipped with an ultrasonic nozzle (Sono-Tek, 120 kHz). A biodegradable polymer, RG503H (Boehringer-Ingelheim, Germany), and a drug, leuprorelin acetate (Polypeptide Laboratories, Denmark), were used. 50 g of RG503H and 2.5 g of leuprorelin acetate were homogeneously dissolved in 500 ml of glacial acetic acid (Yakuri Pure Chemicals, Japan). The solution was transported at a flow rate of 3 ml/min using a piston pump. The transported solution was sprayed into the spray dryer through an ultrasonic nozzle installed in an upper part of a dryer, and dried with drying air at 200° C. Thereafter, microspheres recovered from a cyclone were taken in a certain volume, weighed precisely, added at a concentration of 50 mg/ml to an aqueous solution containing distilled water and 1% (w/v) of a dispersing agent, and suspended therein for one hour at room temperature using a magnetic agitator. Dispersing agents used included polyvinyl alcohol (Sigma, P-8136), polyvinylpyrrolidone (Sigma, PVP-360), human serum albumin (Sigma, A-1654), polyethylene glycol (Yakuri Pure Chemicals, 28123), Tween 80 (Sigma, P-0343), poloxamer (Sigma, P-1300), sodium carboxymethylcellulose (Sigma, C-5678), gelatin (Sigma, G-6650), glycine (Sigma, G-7126), and mannitol (Sigma, M-8429). The suspension was passed through a vacuum filter. Microspheres thus collected were washed with distilled water two times and freeze-dried.

Test Example 1: Evaluation of Recovery Rates and Syringeability of Microspheres

The microspheres prepared in Preparation Example 1 were dispersed in an aqueous solution, and assessed for recovery rates into a syringe and syringeability. Each microsphere formulation was placed into a beaker, and mixed with triple distilled water at a concentration of 50 mg/ml. When microspheres were homogenously dispersed using a magnetic agitator, 1 ml of the dispersion was finely withdrawn into a 1-ml syringe fitted with a 21 gauge needle (n=20). 1 ml of the microsphere suspension in the syringe was transferred into a 1.5-ml Eppendorff tube and freeze-dried. Microspheres recovered into the Eppendorff tube were assessed for dry weight, and the results are given in Table 1, below.

TABLE 1

Recovery rates of microspheres according to the type of dispersing agents

| Type of dispersing agents | Recovery rates (%) | RSD (%) |
|---|---|---|
| Microspheres immediately after spray drying | 11.4 | 17.9 |
| Distilled water | 22.7 | 13.4 |
| Polyvinyl alcohol | 91.5 | 4.2 |
| Polyvinylpyrrolidone | 51.6 | 24.4 |
| Human serum albumin | 70.1 | 36.4 |
| Polyethylene glycol | 66.8 | 19.0 |
| Tween 80 | 68.8 | 30.3 |
| Poloxamer | 24.2 | 56.8 |
| Sodium carboxymethylcellulose | 60.9 | 16.9 |
| Gelatin | 75.7 | 11.0 |

TABLE 1-continued

Recovery rates of microspheres according
to the type of dispersing agents

| Type of dispersing agents | Recovery rates (%) | RSD (%) |
|---|---|---|
| Glycine | 44.7 | 39.0 |
| Mannitol | 46.5 | 25.5 |

Note:
RSD (relative standard deviation = [standard deviation of weight of recovered microspheres/mean] × 100) indicates the deviation of recovered mass.

As apparent in Table 1, microspheres immediately after spray drying, which did not undergo a dispersion process, and microspheres that underwent a dispersion process in distilled water not containing a dispersing agent were found to decrease with respect to recovery rate and homogeneity when withdrawn into a syringe and injected from the syringe. Among several dispersing agents mentioned in the literature studies, polyvinyl alcohol exhibited the highest recovery rate, followed by gelatin, human serum albumin and Tween 80. FIG. 1*a* shows the recovery rates and homogeneity of microspheres, which did not undergo a dispersion process or underwent a dispersion process using mannitol and polyvinyl alcohol as dispersing agents, when a microsphere suspension was drawn into a syringe and injected from the syringe into a tube. FIG. 1*b* shows the deviation in each tube for the mean recovery rate in a syringe when microspheres did not undergo a dispersion process or underwent a dispersion process using polyvinyl alcohol as a dispersing agent. As shown in FIGS. 1*a* and 1*b*, microspheres had the highest recovery rate and the best homogeneity when undergoing a dispersion process using polyvinyl alcohol.

Preparation Example 2: An Effect of Dispersion Time for Improving the Dispersibility of Microspheres PLGA microspheres were prepared using a spray dryer (SODEVA, France) equipped with an ultrasonic nozzle (Sono-Tek, 120 kHz). A biodegradable polymer, RG503H, and a drug, leuprorelin acetate, were used. 40 g of RG503H and 4 g of leuprorelin acetate were homogeneously dissolved in 400 ml of glacial acetic acid. The solution was sprayed into a spray dryer through an ultrasonic nozzle at a flow rate of 3 ml/min, and dried with drying air at 200° C. Thereafter, microspheres recovered from a cyclone were taken in a predetermined amount, added at a concentration of 50 mg/ml to an aqueous solution containing 1% (w/v) polyvinyl alcohol, and suspended therein for 1 min, 3 min, 5 min, 10 min, 1 hr, 3 hr and 6 hr at 25° C. using a magnetic agitator. The suspension was passed through a vacuum filter. Microspheres thus collected were washed with distilled water two times, and freeze-dried.

Test Example 2: Evaluation of Recovery Rates and Syringeability of Microspheres The microspheres prepared in Preparation Example 2 were dispersed in an aqueous solution, and assessed for recovery rates into a syringe and syringeability. This test was performed according to the same method as in Test Example 1, and the results are given in Table 2, below.

TABLE 2

| Recovery rates of microspheres according to dispersion time | | | | | | | |
|---|---|---|---|---|---|---|---|
| | 1 min | 3 min | 5 min | 10 min | 1 hr | 3 hr | 6 hr |
| Recovery rates (%) | 71.4 | 80.0 | 86.1 | 89.6 | 89.4 | 90.2 | 90.3 |
| RSD (%) | 13.6 | 11.6 | 7.8 | 5.5 | 5.9 | 4.9 | 4.8 |

As apparent in Table 2, a high recovery rate was observed immediately after microspheres were suspended in a polyvinyl alcohol solution. As the dispersion time was extended, microspheres exhibited increased recovery rates and homogeneity when withdrawn into a syringe and injected from the syringe. However, after a certain suspension time, the recovery rates and homogeneity were maintained at constant levels.

Test Example 3: Measurement of Residual Polyvinyl Alcohol Content

The microspheres prepared in Preparation Example 2 were assessed for residual polyvinyl alcohol content. This assay was performed by modifying a method described in Journal of Controlled Release, 82 (2002), 105-114, as follows. 2 mg of a formulation, which was accurately weighed, were placed into a glass vial, mixed with 400 μl of 0.5 N NaOH, and allowed to react in an oven at 60° C. for 2-3 hrs to be completely dissolved (n=3). The solution, in which microspheres were completely dissolved, was neutralized with 180 μl of 1 N HCl, supplemented with 600 μl of 0.65 M boric acid and 100 μl of an $I_2$/KI (0.05 M/0.15 M) solution, and allowed to react for 20 min. Then, absorbance was measured at 690 nm (UV). The results are given in Table 3, below.

TABLE 3

| Residual polyvinyl alcohol amounts according to dispersion time | | | | | | | |
|---|---|---|---|---|---|---|---|
| | 1 min | 3 min | 5 min | 10 min | 1 hr | 3 hr | 6 hr |
| Residual amount (w/w) | 0.02 | 0.04 | 0.05 | 0.07 | 0.12 | 0.22 | 0.38 |

As shown in Table 3, the residual amounts of polyvinyl alcohol increased as the suspension time in the polyvinyl alcohol solution increased.

When the results shown in Tables 2 and 3 were taken together, the dispersibility and recovery rates of microspheres improved immediately after microspheres were suspended and dispersed in an aqueous solution of polyvinyl alcohol, but a dispersion time of about 5 min or longer was needed for the optimal effect. In this case, the amount of polyvinyl alcohol remaining on the surface of microspheres was more than 0.05 wt %. This is a critical factor in determining the recovery rate of microspheres.

Comparative Preparation Example 1: Preparation of Microspheres by Co-Spraying with Polyvinyl Alcohol PLGA microspheres were prepared using a spray dryer (SODEVA, France) equipped with an ultrasonic nozzle (Sono-Tek, 120 kHz). A biodegradable polymer, RG503H, and a drug, leuprorelin acetate, were used. To prepare a control microsphere formulation, 1.8 g of RG503H and 0.2 g of leuprorelin acetate were homogeneously dissolved in 90 ml of glacial acetic acid. The solution was transported at a flow rate of 1.5 ml/min using a piston pump. The transported solution was sprayed into the spray dryer through an ultrasonic nozzle installed at an upper part of a dryer, and dried with drying air at 200° C. Thereafter, microspheres recovered from a cyclone were taken in a predetermined amount, added at a concentration of 50 mg/ml to an aqueous solution containing 1% (w/v) polyvinyl alcohol as a dispersing agent, and suspended therein for 1 hr at room temperature using a magnetic agitator. The suspension was passed through a vacuum filter. Microspheres thus collected were washed with distilled water two times and freeze-dried.

A comparative microsphere formulation was prepared by spray drying microspheres and polyvinyl alcohol at the same time in order to compare the dispersion effect of co-spray dried polyvinyl alcohol with that in the control formulation. 1.8 g of RG503H and 0.2 g of leuprorelin acetate were homogeneously dissolved in 90 ml of glacial acetic acid. The solution was transported at a flow rate of 1.5 ml/min using a piston pump. The transported solution was sprayed into the spray dryer through an ultrasonic nozzle installed at an upper part of a dryer, and dried with drying air at 200° C., thereby yielding a comparative formulation.

The control and comparative microsphere formulations prepared as described above were individually dispersed in an aqueous solution, and assessed for recovery rates into a syringe and syringeability. This assay was performed according to the same method as in Test Example 1, and final dry weights of microspheres in tubes were measured. The results are given in Table 4, below. The residual polyvinyl alcohol amount of each microsphere formulation was determined according to the same method as in Test Example 3.

An in vitro release test was carried out, as follows. 10 mg of each microsphere formulation were placed into a 1.5-ml tube, mixed with 1 ml of phosphate buffered saline (PBS), and incubated for 1 hr in an incubator at 37° C. with agitation at 5 rpm using a rotary shaker (SLRM-2M, Seoulin Bioscience). Each reaction solution was centrifuged, and the supernatant was assessed for the amounts of the peptide drug released from microspheres using a fluorescence detector (Varian, Cary Eclipse; Ex: 280 nm, Em: 350 nm)

TABLE 4

Dispersibility, residual polyvinyl alcohol amounts and initial drug release of control and comparative microsphere formulations

| Formulation | Residual polyvinyl alcohol (%) | Initial drug release (%) | Recovery rate (%) | RSD (%) |
|---|---|---|---|---|
| Control | 0.13 | 3.1 | 75.32 | 5.62 |
| Comparative | 0.52 | 15.5 | 68.18 | 13.13 |

As shown in Table 4, compared to the control microsphere formulation undergoing a dispersion process using polyvinyl alcohol, the comparative microsphere formulation not undergoing a suspending process had a high residual polyvinyl alcohol concentration, but exhibited decreased recovery rate and homogeneity when withdrawn into a syringe and injected therefrom, and a high initial drug release rate.

Preparation Example 3: Effect of Polyvinyl Alcohol Suspension Temperature on Drug Loss PLGA microspheres were prepared using a spray dryer (SODEVA, France) equipped with an ultrasonic nozzle (Sono-Tek, 120 kHz). A biodegradable polymer, RG502H, and a drug, leuprorelin acetate, were used. 6.16 g of RG502H and 0.84 g of leuprorelin acetate were homogeneously dissolved in 41 ml of glacial acetic acid. The solution was sprayed into a spray dryer through an ultrasonic nozzle at a flow rate of 3 ml/min, and dried with dry air at 200° C. Thereafter, microspheres recovered from a cyclone were taken in a predetermined amount, added at a concentration of 40 mg/ml to an aqueous solution containing 1% (w/v) polyvinyl alcohol, and suspended therein for 60 min at various temperature conditions of 5, 15, 25, 35, 45° C. using a magnetic agitator. The suspension was passed through a vacuum filter. Microspheres thus collected were washed with distilled water two times, and freeze-dried.

Test Example 4: Evaluation of the Drug Loss During Polyvinyl Alcohol Suspension Step The drug losses were determined using HPLC by measuring leuprorelin in PLGA microspheres obtained according to the above Preparation Example and suspension filtrates. HPLC was carried out using a C18 column (5 μm, 4.6×150 mm). A mixture of acetonitrile (Burdick & Jackson, Cat No. AH015-4) and 100 mM ammonium dihydrogen phosphate (pH 7.0) was used as a mobile phase with a flow rate of 750 μl/min. Leuprorelin was detected at 220 nm (UV), and the results are given in the following Table.

TABLE 5

Drug loss during polyvinyl alcohol suspension step

| PVA suspension temperature (° C.) | Percent of drug recovered: Filtrate | Percent of drug recovered: Microspheres | Mass Balance |
|---|---|---|---|
| After Spray drying (without suspension) | — | 100.00 | 100.00 |
| 5 | 2.87 | 96.62 | 99.49 |
| 15 | 3.00 | 95.49 | 98.49 |
| 25 | 5.15 | 93.82 | 98.97 |
| 35 | 15.89 | 85.05 | 100.94 |
| 45 | 30.72 | 71.28 | 102.00 |

As shown in the above Table, the drug loss from microspheres during the polyvinyl alcohol suspension step was increased with the increasing temperature of the suspension. Particularly, the temperature of 45° C. was not appropriate for the production of the sustained release formulation because the drug loss was too high.

Test Example 5: Evaluation of Residual Solvent Removal Rates According to Time of Dispersion Using Polyvinyl Alcohol Microspheres were prepared and recovered from a cyclone according to the same method as in Preparation Example 2, and suspended in an aqueous solution of 1% polyvinyl alcohol at a concentration of 50 mg/ml. While the aqueous solution was maintained at 25° C., the removal rates of residual acetic acid were measured at given time points. The concentrations of residual acetic acid in microspheres were determined as follows. Microspheres were dissolved in methylene chloride (Junsei, 34355-0350), supplemented with an aqueous solution of 0.07% phosphoric acid (Sigma, P-6560), and vigorously mixed therewith. The mixture was centrifuged to separate a layer of the aqueous phosphoric acid solution. This layer was recovered and assessed for the amount of acetic acid using HPLC. HPLC was carried out using a C18 column (5 μm, 4.6×250 mm, 120 Å). A mixture of 5-50% linear gradient of methanol (J. T. Baker, AH230-4)

and 0.07% phosphate buffer (pH 3.0) was used as a mobile phase having a flow rate of 1.2 ml/min. Acetic acid was detected at 210 nm (UV), and the results are given in Table 6, below. The residual acetic acid content immediately after microspheres were prepared was 0.8 wt %.

TABLE 6

Residual solvent removal rates according to dispersion time

| Time (min) | Acetic acid removal rates (%) |
|---|---|
| 5 | 20.0 |
| 10 | 34.2 |
| 20 | 44.0 |
| 40 | 54.5 |
| 60 | 61.3 |
| 120 | 73.6 |
| 180 | 87.9 |

As shown in Table 6, the residual solvent removal rates gradually increased with increasing time of suspension of microspheres in an aqueous solution of polyvinyl alcohol to remove the residual solvent. The final residual solvent was maintained at less than 0.1 wt %.

Preparation Example 4: Preparation of BSA-Loaded Microspheres by Spray Drying of W/O Type Emulsion Containing BSA 0.5 g of bovine serum albumin (BSA) (Sigma, A-7638) was dissolved in distilled water, and homogeneously mixed with a solution prepared by dissolving 9.5 g of RG502H in 95 ml of methylene chloride, thereby yielding a W/O type emulsion. While the emulsion was maintained in an emulsion state using an agitator, it was supplied to a spray dryer (Buchi-191) at a flow rate of 3 ml/min. Compressed air was supplied to a two-fluid nozzle at a flow rate of 450 NL/h to dry sprayed atomized droplets using drying air at 80° C. The recovered microspheres were suspended for 3 hrs in an aqueous solution of 1% polyvinyl alcohol at a concentration of 50 mg/ml with agitation using a magnetic agitator, washed with distilled water, and freeze-dried. The microspheres thus prepared had a mean particle size of 5.2 μm, and the amount of polyvinyl alcohol remaining on the surface of the microspheres was 0.93% (w/w).

Preparation Example 5: Preparation of BSA-Loaded Microspheres by Spray Drying of S/O Type Suspension Containing BSA 1 g of BSA was finely pulverized in a mortar, and homogeneously mixed with a solution prepared by dissolving 9 g of RG502H in 90 ml of methylene chloride, thereby yielding an S/O type suspension. While the suspension was maintained in a suspension state using an agitator, it was supplied to a spray dryer (Buchi-191) at a flow rate of 3 ml/min. Compressed air was supplied to a two-fluid nozzle at a flow rate of 450 NL/h to dry sprayed atomized droplets using drying air at 80° C. The recovered microspheres were suspended for 3 hrs in an aqueous solution of 1% polyvinyl alcohol at a concentration of 50 mg/ml with agitation using a magnetic agitator, washed with distilled water, and freeze-dried. The microspheres thus prepared had a mean particle size of 5.8 μm, and the amount of polyvinyl alcohol remaining on the surface of the microspheres was 0.85% (w/w).

Preparation Example 6: Preparation of Leuprorelin-Loaded Microspheres 1 g of leuprorelin acetate and 9 g of RG502H were dissolved in 90 ml of glacial acetic acid. The solution was supplied to a spray dryer (Buchi-191) at a flow rate of 2 ml/min. Compressed air was supplied to a two-fluid nozzle at a flow rate of 500 NL/h to dry sprayed atomized droplets using drying air at 120° C. The recovered microspheres were suspended for 3 hrs in an aqueous solution of 1% polyvinyl alcohol at a concentration of 50 mg/ml with agitation using a magnetic agitator, washed with distilled water, and freeze-dried. The microspheres thus prepared had a mean particle size of 5.1 μm, and the amount of polyvinyl alcohol remaining on the surface of the microspheres was 0.98% (w/w).

Preparation Example 7: Preparation of Leuprorelin-Loaded Microspheres 0.4 g of leuprorelin acetate and 9.6 g of R202H were dissolved in 96 ml of glacial acetic acid. The solution was supplied to a spray dryer (SODEVA, France) at a flow rate of 3 ml/min, sprayed into a dry chamber using an ultrasonic nozzle (Sono-Tek, 120 kHz), and dried using drying air at 200° C. The recovered microspheres were suspended for 3 hrs in an aqueous solution of 1% polyvinyl alcohol at a concentration of 50 mg/ml with agitation using a magnetic agitator, washed with distilled water, and freeze-dried. The microspheres thus prepared had a mean particle size of 23.4 μm, and the amount of polyvinyl alcohol remaining on the surface of the microspheres was 0.16% (w/w).

Preparation Example 8: Preparation of Leuprorelin-Loaded Microspheres 0.5 g of leuprorelin acetate and 9.5 g of R202H were dissolved in 95 ml of glacial acetic acid. The solution was supplied to a spray dryer (SODEVA, France) at a flow rate of 3 ml/min, sprayed into a dry chamber using an ultrasonic nozzle (Sono-Tek, 60 kHz), and dried using drying air at 200° C. The recovered microspheres were suspended for 3 hrs in an aqueous solution of 1% polyvinyl alcohol at a concentration of 50 mg/ml with agitation using a magnetic agitator, washed with distilled water, and freeze-dried. The microspheres thus prepared had a mean particle size of 32.6 μm, and the amount of polyvinyl alcohol remaining on the surface of the microspheres was 0.11% (w/w).

Preparation Example 9: Preparation of Leuprorelin-Loaded Microspheres 1.4 g of leuprorelin acetate, 0.86 g of RG504H and 7.74 g of R202H were dissolved in 86 ml of glacial acetic acid. The solution was supplied to a spray dryer (SODEVA, France) at a flow rate of 3 ml/min, sprayed into a dry chamber using an ultrasonic nozzle (Sono-Tek, 120 kHz), and dried using drying air at 200° C. The recovered microspheres were suspended for 90 min in an aqueous solution of 1% polyvinyl alcohol at a concentration of 50 mg/ml with agitation using a magnetic agitator, washed with distilled water, and freeze-dried.

Preparation Example 10: Preparation of Octreotide-Loaded Microspheres 0.7 g of octreotide acetate and 9.3 g of RG502H were dissolved in 186 ml of glacial acetic acid. The solution was supplied to a spray dryer (SODEVA, France) at a flow rate of 3 ml/min, sprayed into a dry chamber using an ultrasonic nozzle (Sono-Tek, 120 kHz), and dried using drying air at 200° C. The recovered microspheres were suspended for 1 hr in an aqueous solution of 1% polyvinyl alcohol at a concentration of 50 mg/ml with agitation using a magnetic agitator, washed with distilled water, and freeze-dried.

Test Example 6

Figure 1A:
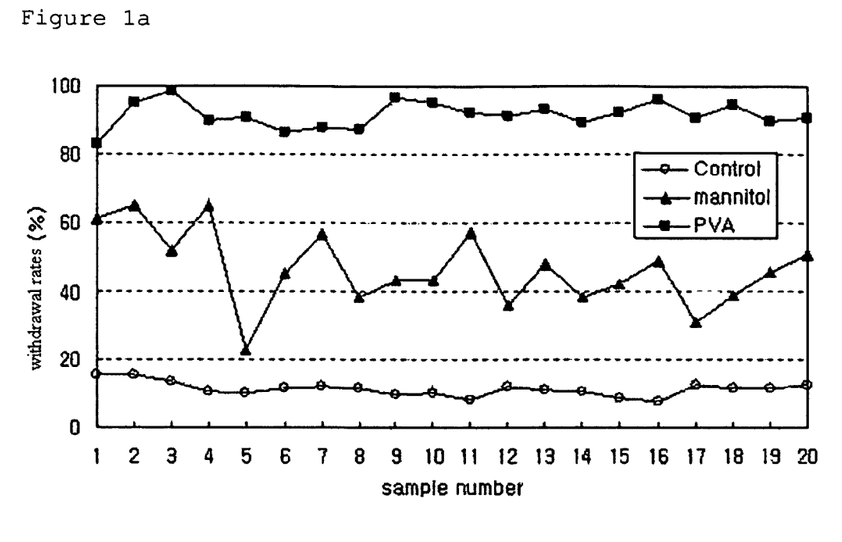
FIGS. 1a and 1b show the dispersion/recovery rates and syringeability of microspheres prepared in Preparation Example 1 according to the present invention in an aqueous solution, wherein, after a test was carried out according to the method described in Test Example 1, the recovery rates of microspheres in each tube (FIG. 1a) and the deviation in each tube for the mean recovery rate (FIG. 1b) were measured.
Figure 1B:
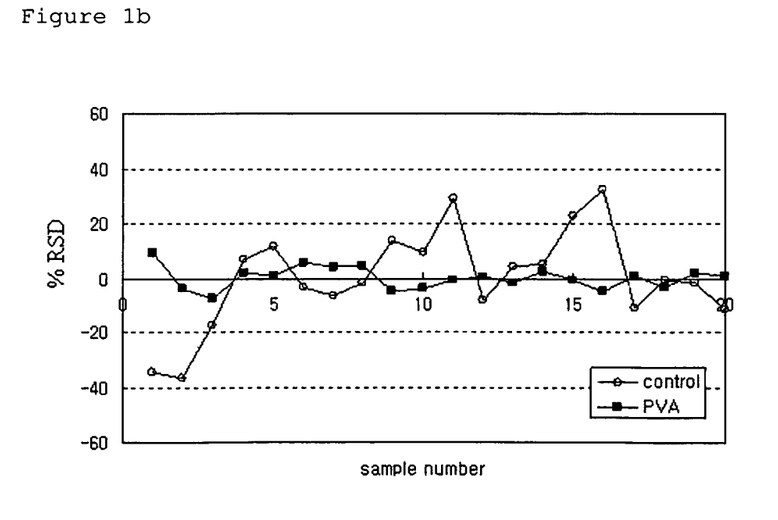
Figure 2:
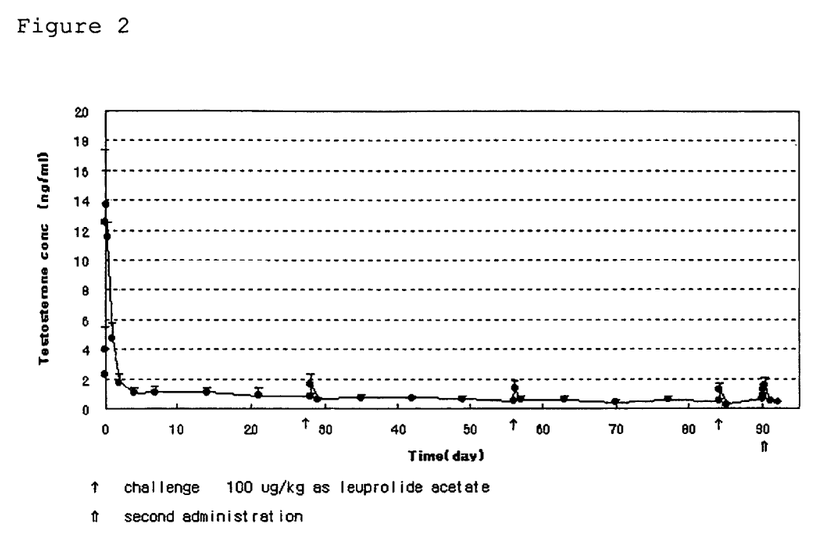
FIG. 2 shows the serum testosterone concentrations in male SD rats (n=5) which were subcutaneously injected as described for Test Example 5 with a single dosage of leuprorelin-loaded microspheres prepared in Preparation Example 8.

The leuprorelin-loaded microspheres prepared in Preparation Example 9 was suspended in a suspension (0.5% (w/w) sodium carboxymethylcellulose, 5% (w/w) mannitol, 0.1% Tween 80), and subcutaneously injected at a single dosage of 9 mg/kg (leuprorelin acetate) into male SD rats (n=5, 195±20 g). Blood samples were collected from tail veins before drug administration, 30 min, 1 hr, 3 hr, 6 hr and 1, 2, 4 and 7 days after drug administration, and every seven days for a period from day 8 to 90. Rats were challenged with an injection of aqueous leuprorelin acetate solution at a dosage of 100 μg/kg at 28, 56 and 84 days after drug administration in order to evaluate the sustained release of the drug from the microspheres, and blood samples were collected before and 3 and 24 hrs after challenge. Second drug administration was carried out 90 days after the first drug administration, and blood samples were collected as described in the first drug administration. The collected blood samples were placed into 1.5-ml Eppendorff tubes, and centrifuged for 10 min at 4° C. and 12,000 rpm. The obtained sera were stored at −20° C. Serum testosterone levels were measured using a radio-immunoassay (RIA) Kit (DSL-10-4000, Diagnostic Systems Laboratories, Inc., Webster, Tex., USA), and the results are given in FIG. 2. The three challenges, which were performed every 28 days after drug administration, and the second drug administration, which was performed 90 days after drug administration, resulted in inhibition of the rise of serum testosterone levels. These results indicate that leuprorelin was continuously released over the test period of 90 days.

Test Example 7

Figure 3:
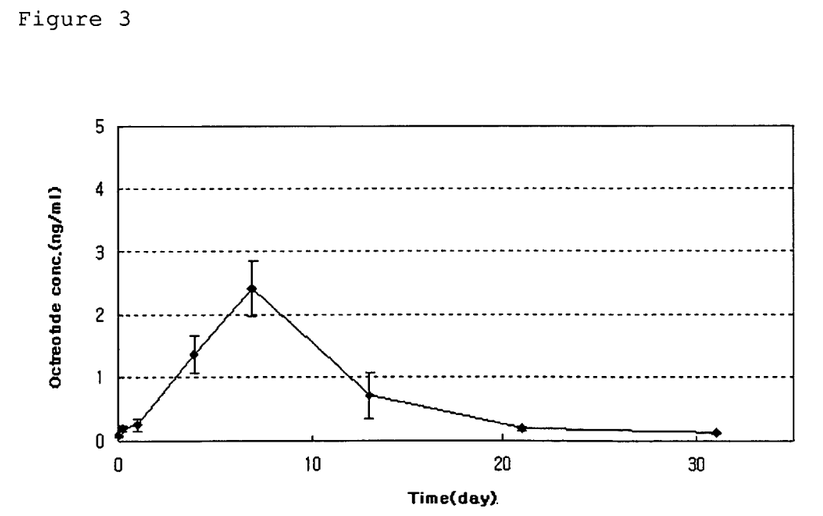
FIG. 3 shows the serum octreotide concentrations in male SD rats (n=6) which were subcutaneously injected as described for Test Example 6 with a single dosage of octreotide-loaded microspheres prepared in Preparation Example 9.

The octreotide-loaded microspheres prepared in Preparation Example 10 were suspended in a suspension (0.5% (w/w) sodium carboxymethylcellulose, 0.6% (w/w) mannitol), and subcutaneously injected at a single dosage of 5 mg/kg (octreotide) to male SD rats (n=6, 195±20 g). Blood samples were collected from tail veins before drug administration and 6 hrs and 1, 4, 7, 13, 21 and 31 days after drug administration. The collected blood samples were placed into 1.5-ml Eppendorff tubes, and centrifuged for 10 min at 4° C. and 12,000 rpm. The obtained sera were stored at −20° C. Serum octreotide concentrations were measured using an enzyme immunoassay (EIA) kit (Bachem, S-1275, Peninsula Laboratories Inc., USA). The results are given in FIG. 3. As shown in FIG. 3, the octreotide drug was found to be continuously released for a period of more than two weeks.

INDUSTRIAL APPLICABILITY

As described hereinbefore, the process of preparing microspheres according to the present invention allows the preparation of sustained release microspheres not having the problems of conventional preparation methods of sustained release microspheres, including toxicity due to residual solvent and poor syringeability. The microspheres prepared according to the present invention release an effective concentration of a drug in a sustained manner for a predetermined period when administered to the body, prevent rapid initial drug release, and reduce the required administration frequency of a drug. Thus, the present microspheres are useful in the treatment of diseases.

The invention claimed is:
1. A method for removing solvent remaining in a sustained release microsphere and improving suspendability and syringeability of the sustained release microsphere, the method comprising:
  a) dispersing a spray-dried microsphere in an aqueous solution containing 0.05-10 w/v % polyvinyl alcohol over a duration of 5 minutes to 6 hours at room temperature;
  b) removing the spray-dried microsphere from the aqueous solution by filtration;
  c) washing the filtered spray-dried microsphere such that an amount of residual polyvinyl alcohol on the surface of the spray-dried microsphere is in a range of 0.05 to 0.5 w/w %; and
  d) freeze-drying the washed filtered spray-dried microsphere,
wherein the spray-dried microsphere is prepared by spraying a solution, suspension, or emulsion containing a biodegradable polymer, a drug, and glacial acetic acid as a solvent into a dry chamber and drying it with dry air to remove the solvent and generate a spray-dried microsphere, the drug is leuprorelin or octreotide, the biodegradable polymer is one or more selected from the group consisting of polylactide, polyglycolide, poly(lactide-co-glycolide), polyorthoester, polyanhydride, polyhydroxybutyric acid, polycaprolactone, and polyalkylcarbonate.

* * * * *